(12) United States Patent
Hashida et al.

(10) Patent No.: US 9,217,349 B2
(45) Date of Patent: Dec. 22, 2015

(54) CONTROL APPARATUS FOR INTERNAL COMBUSTION ENGINE

(75) Inventors: Tatsuhiro Hashida, Susono (JP); Hiroki Nishijima, Suntou-gun (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 13/819,938

(22) PCT Filed: Oct. 26, 2011

(86) PCT No.: PCT/JP2011/074680
§ 371 (c)(1),
(2), (4) Date: Feb. 28, 2013

(87) PCT Pub. No.: WO2013/061422
PCT Pub. Date: May 2, 2013

(65) Prior Publication Data

US 2014/0216014 A1 Aug. 7, 2014

(51) Int. Cl.
*F01N 3/00* (2006.01)
*F01N 3/20* (2006.01)
(Continued)

(52) U.S. Cl.
CPC .............. *F01N 3/2006* (2013.01); *F01N 3/035* (2013.01); *F01N 3/2066* (2013.01); *F01N 9/002* (2013.01); *F01N 11/00* (2013.01); *F01N 13/009* (2013.01); *F02D 41/1466* (2013.01); *G01N 15/0606* (2013.01); *G01N 15/0656* (2013.01); *F01N 3/023* (2013.01); *F01N 3/0885* (2013.01); *F01N 2430/085* (2013.01); *F01N 2550/04* (2013.01);
(Continued)

(58) Field of Classification Search
CPC ..... F01N 3/0842; F01N 3/2066; F01N 3/035; F01N 13/02; F01N 2610/02; F01N 2610/03; F01N 9/002; F02D 41/0275; F02D 41/1441; F02D 41/0295; F02D 41/029

USPC .................. 60/274, 285, 286, 295, 301, 303; 73/114.69, 114.75
See application file for complete search history.

(56) References Cited

U.S. PATENT DOCUMENTS

2002/0078681 A1* 6/2002 Carberry et al. ................. 60/280
2008/0307770 A1* 12/2008 Brahma et al. .................. 60/273
(Continued)

FOREIGN PATENT DOCUMENTS

JP 2009144577 A * 7/2009
JP A 2009-144577 7/2009
(Continued)

*Primary Examiner* — Patrick Maines
(74) *Attorney, Agent, or Firm* — Oliff PLC

(57) ABSTRACT

An internal combustion engine includes an SCR system disposed on an exhaust passage and a particulate matter sensor disposed downstream of the SCR system, the particulate matter sensor for producing an output that corresponds to an amount of particulate matter deposited on an element section. A control apparatus for the internal combustion engine includes: means for detecting a condition of the element section being deposited with a urea-related substance; and means for controlling to bring a temperature of the element section to a first temperature range when the condition of being deposited with the urea-related substance is detected. The first temperature range is higher than a temperature at which the urea-related substance vaporizes and lower than a temperature at which the particulate matter burns. This prevents the urea-related substance from being deposited on an electrode of the particulate matter sensor and limits variations in an output of the particulate matter sensor.

13 Claims, 6 Drawing Sheets

(51) Int. Cl.
*G01N 15/06* (2006.01)
*F01N 9/00* (2006.01)
*F01N 11/00* (2006.01)
*F02D 41/14* (2006.01)
*F01N 13/00* (2010.01)
*F01N 3/035* (2006.01)
*F01N 3/023* (2006.01)
*F01N 3/08* (2006.01)
*G01N 15/00* (2006.01)

(52) U.S. Cl.
CPC ......... *F01N 2560/05* (2013.01); *F01N 2610/02* (2013.01); *F02D 41/1494* (2013.01); *G01N 2015/0046* (2013.01); *Y02T 10/24* (2013.01); *Y02T 10/47* (2013.01)

(56) References Cited

U.S. PATENT DOCUMENTS

| | | | |
|---|---|---|---|
| 2009/0056310 A1* | 3/2009 | Xu et al. | 60/274 |
| 2011/0239623 A1* | 10/2011 | Leustek et al. | 60/274 |
| 2012/0090582 A1* | 4/2012 | Yacoub | 123/568.11 |
| 2012/0227377 A1* | 9/2012 | Hopka et al. | 60/274 |
| 2014/0230415 A1* | 8/2014 | Shimode et al. | 60/286 |
| 2014/0366511 A1* | 12/2014 | Hashida et al. | 60/277 |

FOREIGN PATENT DOCUMENTS

| | | | | |
|---|---|---|---|---|
| JP | 2012189049 A | * | 10/2012 | |
| JP | 2013087653 A | * | 5/2013 | |
| WO | WO 2007132334 A2 | * | 11/2007 | G01N 1/22 |
| WO | WO 2014076818 A1 | * | 5/2014 | |

* cited by examiner

CONTROL APPARATUS FOR INTERNAL COMBUSTION ENGINE

TECHNICAL FIELD

The present invention relates to control apparatuses for internal combustion engines. More specifically, the present invention relates to a control apparatus for an internal combustion engine including a particulate matter sensor.

BACKGROUND ART

A system disclosed in patent document 1, for example, includes a particulate matter sensor (PM sensor) for detecting particulate matter (hereinafter referred to also as "PM") in an exhaust passage of an internal combustion engine. The PM sensor includes an insulating substrate and a pair of electrodes disposed on the insulating substrate with a space between the electrodes. When PM in an exhaust gas deposits between the electrodes of the PM sensor, conductivity across the electrodes changes according to an amount of PM deposited. This varies resistance across the electrodes. Detection of a value of the resistance across the electrodes of the PM sensor therefore allows an amount of PM contained in the exhaust gas associated with the amount of PM deposited between the electrodes to be detected.

In the technique disclosed in patent document 1, the PM sensor is disposed downstream of a particulate matter trapping filter (diesel particulate filter, hereinafter referred to also as a "DPF"). In patent document 1, the amount of PM discharged downstream of the DPF is detected based on the value of the resistance across the electrodes of the PM sensor, so that, for example, a determination is made as to whether the DPF is faulty.

PRIOR ART DOCUMENTS

Patent Document

Patent Document 1: JP-A-2009-144577

SUMMARY OF THE INVENTION

Problem to be Solved by the Invention

A known arrangement includes a urea selective catalytic reduction (SCR) system disposed on the exhaust passage of an internal combustion engine for purifying NOx and a PM sensor disposed downstream of the SCR system. In the SCR system, a urea aqueous solution is injected into the exhaust passage and ammonia produced from the urea aqueous solution is supplied to a catalyst, so that NOx is reduced.

However, the urea and a urea-derived substance (hereinafter referred to also as a "urea-related substance" including the urea and the urea-derived substance) supplied flow through the SCR system and are discharged to a downstream side and may deposit on the electrodes of the PM sensor. In such a case, if the urea-related substance deposited has conductivity, it greatly changes the value of the resistance across the electrodes of the PM sensor. This is likely to vary an output of the PM sensor. The variations in the output of the PM sensor are not desirable, because, for example, a situation may result in which a false determination is made as to whether the DPF is faulty.

The present invention has been made to solve the foregoing problem and it is an object of the present invention to provide an improved control apparatus for an internal combustion engine that can detect a PM amount and determine a DPF fault with even higher accuracy by limiting deposition of a urea-related substance on an electrode of a PM sensor.

Means for Solving the Problem

To achieve the foregoing object, an aspect of the present invention provides a control apparatus for an internal combustion engine. The internal combustion engine includes an SCR system disposed on an exhaust passage; and a particulate matter sensor disposed downstream of the SCR system, the particulate matter sensor for producing an output that corresponds to an amount of particulate matter deposited on an element section. The control apparatus for an internal combustion engine according to the aspect of the present invention includes: means for detecting a condition of the element section being deposited with a urea-related substance; and means for controlling to bring a temperature of the element section to a first temperature range when the condition of being deposited with the urea-related substance is detected. The first temperature range is higher than a temperature at which the urea-related substance vaporizes and lower than a temperature at which the particulate matter burns. The "urea-related substance" includes urea and a substance derived from the urea.

The detecting means preferably detects the condition of being deposited with the urea-related substance based on an amount of change in an output of the particulate matter sensor.

The control apparatus according to the aspect of the present invention, further preferably comprises means for performing a process for removing particulate matter deposited on a catalyst of the SCR system when the condition of being deposited with the urea-related substance is detected.

If the control apparatus according to the aspect of the present invention is to control an internal combustion engine further including a filter disposed upstream of the particulate matter sensor along the exhaust passage, the filter for trapping particulate matter contained in an exhaust gas, preferably the removal means removes particulate matter deposited on the catalyst by performing a process for removing particulate matter accumulated on the particulate matter trapping filter.

The removal means preferably removes the particulate matter by performing a control of increasing a temperature of the exhaust gas of the internal combustion engine.

The removal means preferably performs the process for removing the particulate matter when the detecting means detects the condition of being deposited with the urea-related substance a plurality of times consecutively.

If the control apparatus according to the aspect of the present invention is to control an internal combustion engine further including a filter disposed upstream of the particulate matter sensor along the exhaust passage, the filter for trapping particulate matter contained in an exhaust gas, preferably the control apparatus further comprises means for determining whether the particulate matter trapping filter is faulty based on the output of the particulate matter sensor. If the detecting means has detected the condition of being deposited with the urea-related substance last time, the temperature control means increases a temperature of the element section so as to fall within the first temperature range when the fault determination is to be made this time. In this case, the determining means determines whether the particulate matter trapping filter is faulty under a condition in which the temperature of the element section is controlled to fall within the first temperature range.

If the control apparatus according to the aspect of the present invention is to control an internal combustion engine further including a filter disposed upstream of the particulate matter sensor along the exhaust passage, the filter for trapping particulate matter contained in an exhaust gas, preferably the control apparatus further comprises means for determining whether the particulate matter trapping filter is faulty based on the output of the particulate matter sensor. If the particulate matter trapping filter has been determined to be faulty last time, the temperature control means increases a temperature of the element section so as to fall within the first temperature range when the particulate matter trapping filter is to be determined to be faulty or not this time. In this case, the determining means determines whether the particulate matter trapping filter is faulty this time under a condition in which the temperature of the element section is controlled to fall within the first temperature range.

The temperature control means according to the aspect of the present invention, when a predetermined operating condition in which the urea-related substance is discharged is detected, preferably controls to bring the temperature of the element section to a temperature that falls outside a urea liquidus temperature range and a biuret decomposition temperature range and is lower than the temperature at which the particulate matter burns.

Alternatively, to achieve the foregoing object, another aspect of the present invention provides a control apparatus for an internal combustion engine. The internal combustion engine according to another aspect of the present invention includes an SCR system disposed on an exhaust passage; and a particulate matter sensor disposed downstream of the SCR system, the particulate matter sensor for producing an output that corresponds to an amount of particulate matter deposited on an element section. The control apparatus for an internal combustion engine according to another aspect of the present invention controls, when a predetermined operating condition in which the urea-related substance is discharged to the exhaust passage is detected, to bring a temperature of the element section to a temperature that falls outside a urea liquidus temperature range and a biuret decomposition temperature range and is lower than a temperature at which particulate matter burns.

Effects of the Invention

If the urea-related substance discharged downstream of the SCR system is deposited on the element section, the output of the PM sensor changes sharply, so that the amount of particulate matter may not be correctly detected. According to an arrangement of the present invention, the temperature of the element section is increased to fall within the first temperature range when the condition of being deposited with the urea-related substance is detected. The temperature control allows the urea-related substance deposited on the element section to be removed. Variations in the output of the PM sensor involved with the discharge of the urea-related substance can therefore be limited.

According to another arrangement in which deposition of the urea-related substance is detected based on the amount of change in the sensor output, the sensor can be determined to be faulty or fully operational without having to incorporate any additional special part.

In still another arrangement in which the particulate matter deposited on the catalyst of the SCR system is to be removed when the condition of being deposited with the urea-related substance is detected, the purification performance of the SCR catalyst can be recovered, which allows discharge of the urea-related substance to a downstream side of the SCR system to be prevented.

In a further arrangement in which, if the condition of being deposited with the urea-related substance is detected last time, or if the particulate matter trapping filter has been determined to be faulty last time, the temperature of the element section is increased so as to fall within the first temperature range when the fault determination is to be made this time, the result of fault determination can be confirmed in a condition in which an effect of the urea-related substance is limited. This allows accuracy in determining a fault of the particulate matter trapping filter to be enhanced.

In a still further arrangement in which the temperature of the element section is brought to a temperature that falls outside a urea liquidus temperature range and a biuret decomposition temperature range in an operating condition in which the urea-related substance is discharged, a type of urea-related substance that is conductive, in particular, of various other types of urea-related substances can be prevented from being deposited in advance, so that variations in the output caused by the deposition of the urea-related substance can be limited.

MODES FOR CARRYING OUT THE INVENTION

Figure 1:
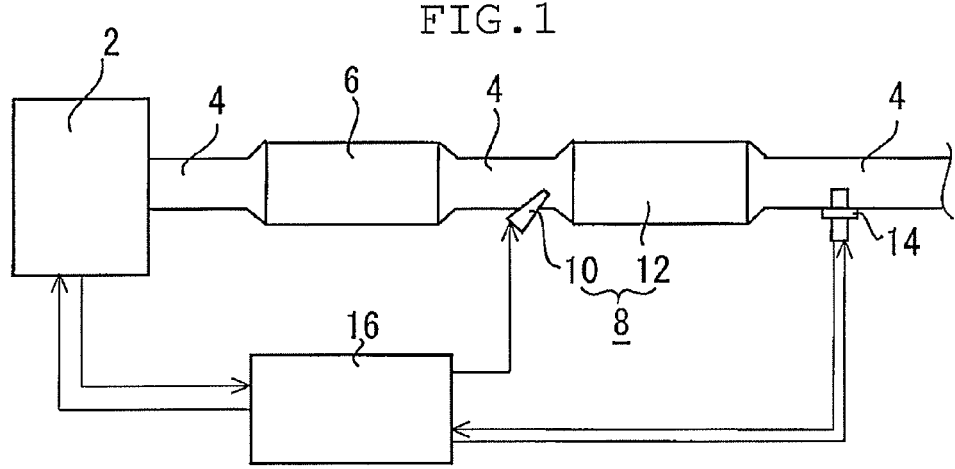
FIG. 1 illustrates a general arrangement of a system according to an embodiment of the present invention.

Embodiments of the present invention will be described below with reference to the accompanying drawings. In each of the drawings, like or corresponding parts are identified by the same reference numerals and descriptions for those parts will be simplified or omitted.

First Embodiment

General Arrangement of System of the First Embodiment

FIG. 1 illustrates a general arrangement of a system according to a first embodiment of the present invention. The system shown in FIG. 1 includes a diesel particulate filter (DPF) 6 as a particulate matter trapping filter disposed on an exhaust passage 4 of an internal combustion engine 2. The DPF 6 traps particulate matter (PM) contained in an exhaust gas.

A urea SCR system 8 (hereinafter referred to also as an "SCR system") is disposed downstream of the DPF 6 on the exhaust passage 4. The SCR system 8 includes a urea aqueous solution injection valve 10 disposed on the exhaust passage 4 and a selective reduction type NOx catalyst 12 (hereinafter referred to also simply as a "NOx catalyst") disposed downstream of the injection valve 10 on the exhaust passage 4. The injection valve 10 is connected to a urea aqueous solution tank not shown. The injection valve 10 injects a urea aqueous solution into the exhaust passage 4 upstream of the NOx catalyst 12. As will be described later, the injected urea aqueous solution is decomposed, which produces ammonia. The NOx catalyst 12 uses the ammonia as a reducing agent to reduce NOx contained in the exhaust gas, thereby purifying the exhaust gas. A PM sensor 14 (particulate matter sensor) is disposed downstream of the NOx catalyst 12.

This system includes a control unit 16. In addition to the PM sensor 14, various other types of sensors for the internal combustion engine 2 are connected to an input side of the control unit 16. An electric circuit of the PM sensor 14, the urea aqueous solution injection valve 10, and various other types of actuators for the internal combustion engine 2 are connected to an output side of the control unit 16. The control unit 16 performs execution of a predetermined program based on input information from the various types of sensors to thereby actuate, for example, the various types of actuators. Various types of control relating to operation of the internal combustion engine 2 are thereby performed.

Figure 2:
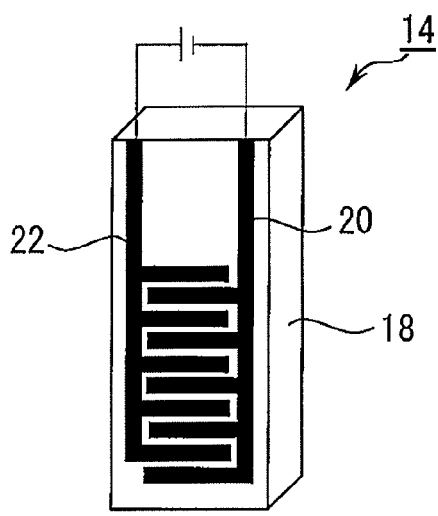
FIG. 2 is a schematic diagram illustrating an arrangement of an element section of the PM sensor according to the embodiment of the present invention.

FIG. 2 is a schematic diagram illustrating an arrangement of an element section of the PM sensor 14 according to the first embodiment. Referring to FIG. 2, the element section of the PM sensor 14 includes an insulating substrate 18. A pair of electrodes 20, 22 is formed on a surface of the insulating substrate 18. The electrodes 20, 22 are disposed in a condition of not in contact with each other, being spaced a predetermined distance apart from each other. Each of the electrodes 20, 22 has a portion formed into a comb-like structure, the comb-like structures being interdigitated with each other. Although, in the first embodiment, each of the electrodes 20, 22 is exemplified as having the comb-like structure, such a structure is not the only possible arrangement; alternatively, the electrodes only need to face each other. A heater not shown is embedded in a lower layer of the electrodes 20, 22 inside the insulating substrate 18.

The electrodes 20, 22 are connected to a power source (not shown) via, for example, an electric circuit. A high voltage is thus applied across the electrode 20 and the electrode 22. In addition, the heater is connected to a power source (not shown) via, for example, an electric circuit. Predetermined electricity is thus supplied to the heater, which results in the element section being heated. The supply of electricity is controlled by the control unit 16.

Outline of Control in the First Embodiment

Types of control performed by the control unit 16 in the first embodiment include detection of a PM amount, resetting of the PM sensor 14, determination of a fault of the DPF 6, and regeneration of the DPF 6, as will be described below.

In the embodiments to be described below, the PM to be trapped by the DPF 6 and to be measured by the PM sensor 14 refers to: substances derived from combustion in the internal combustion engine, such as soot (a soot-like substance including carbon) and soluble organic fraction (SOF); and particulate substances discharged from the internal combustion engine 2 through the operation of the internal combustion engine 2, such as ash derived from a lubricating oil.

(1) Detection of the PM Amount

When a PM discharge amount is to be detected, a "trapping voltage" as the high voltage for trapping the particulate matter is applied across the electrodes 20, 22. The application of the trapping voltage across the electrodes 20, 22 results in PM contained in the exhaust gas being trapped and deposited between the electrodes 20, 22. As the amount of PM deposited between the electrodes 20, 22 increases, a conducting portion between the electrodes 20, 22 increases, which results in a smaller value of resistance across the electrodes 20, 22. An electrical characteristic having a correlation with the resistance across the electrodes 20, 22 is here detected as a sensor output of the PM sensor 14. The amount of PM deposited between the electrodes 20, 22 is considered to vary in association with a change in the amount of PM contained in the exhaust gas. The PM amount in the exhaust gas is therefore detected according to the output of the PM sensor 14. For convenience sake, the embodiments to be described below will be described such that the sensor output increases with an increasing amount of PM deposited between the electrodes 20, 22.

(2) Resetting of PM (Control for Burning to Remove PM)

The output of the PM sensor 14 increases with an increasing amount of PM deposited between the electrodes 20, 22. When the amount of PM deposited between the electrodes 20, 22 reaches a limit value, however, the output of the PM sensor 14 no longer changes. Under this condition, the PM sensor 14 is unable to produce an output that corresponds with the PM amount in the exhaust gas. This requires that the PM deposited on the element section be removed at predetermined timing. This process of removing the PM is also referred to as a "PM reset".

At the PM reset, the control unit 16 supplies the heater of the PM sensor 14 with predetermined electricity to thereby heat, and increase a temperature of, the element section of the PM sensor 14. The PM deposited on the element section of the PM sensor 14 is thereby burned and removed. Preferably, the temperature of the element section of the PM sensor 14 is higher than 500° C. and, more preferably, higher than 700° C. Alternatively, the electricity may be supplied to the heater with a target temperature of the element section during a period of the PM reset set to a value higher than 500° C. and, more preferably, higher than 700° C. Because the PM burns at a temperature of about 500° C. to about 650° C., setting the temperature for the reset to a level of 700° C. or higher (preferably 700° C. to 800° C.) will enhance reliability of combustion of the PM.

(3) Determination of Fault of DPF

If the DPF 6 is faulty, the amount of PM that flows past the DPF 6 to a side downstream thereof increases. The amount of PM deposited between the electrodes 20, 22 of the PM sensor 14 thereby gradually increases with a resultant increase in the sensor output. Specifically, the DPF 6 can be determined to be faulty or not based on the sensor output.

Specifically, in the first embodiment, based on the output of the PM sensor 14 after a lapse of a predetermined period of time after the PM deposited on the element section has been removed through a PM reset, the control unit 16 detects the PM discharge amount discharged downstream of the DPF 6 during the predetermined period of time. Meanwhile, when the DPF 6 remains fully operational, the PM amount estimated to be discharged downstream of the DPF 6 (hereinafter referred to also as an "estimated PM discharge amount") is estimated using a model. The control unit 16 compares the estimated PM amount with the PM discharge amount that is based on the output of the PM sensor 14. If, as a result, the PM discharge amount based on the output of the PM sensor 14 is greater than the estimated PM discharge amount, the DPF 6 is determined to be faulty. It is noted that, in this determination, the estimated PM discharge amount used for the determination represents a value that includes an allowance added so as to take into account, for example, a permissible error.

(4) Regeneration of DPF 6

When the DPF 6 continues trapping PM in the exhaust gas, the amount of PM deposited on the DPF 6 eventually reaches a limit thereof, so that the DPF 6 becomes unable to trap PM any more. To avoid such a condition, when the amount of PM deposited on the DPF 6 reaches a certain level, the PM is burned and removed to thereby regenerate the DPF 6.

Specifically, in a DPF 6 regeneration process, the control unit 16 performs controls for increasing the exhaust temperature according to a predetermined control program, such as, injecting fuel a second time following a first fuel injection sequence and retarding injection timing. This burns to remove the PM deposited on the DPF 6. Such a combustion removal sequence for the PM is performed for a predetermined period of time, which removes a good part of the PM deposited on the DPF 6 to thereby complete regenerating the DPF 6.

Typically, the control unit 16 estimates the PM amount in the exhaust gas discharged from the internal combustion engine 2 using, for example, a model, thereby estimating the amount of PM deposited on the DPF 6. The above-described regeneration process is performed with DPF 6 regeneration timing defined as time when the estimated amount reaches a predetermined amount. In addition, following the regeneration process for the DPF 6, a PM reset is performed in order to remove once PM deposited on the element section.

Control Characteristic of the First Embodiment

The first embodiment includes the SCR system 8 as described earlier. In the SCR system, the urea aqueous solution is injected from the urea aqueous solution injection valve 10 into the exhaust passage 4. A thermal decomposition reaction of formula (1) given below and a hydrolysis reaction of formula (2) given below occurring in the exhaust passage 4 and the NOx catalyst 12 produce ammonia ($NH_3$) from the urea aqueous solution.

$$CO(NH_2)_2 \rightarrow NH_3 + HCNO \quad (1)$$

$$HCNO + H_2O \rightarrow NH_3 + CO_2 \quad (2)$$

The NOx catalyst 12 purifies the exhaust gas by reducing NOx using ammonia produced through decomposition of the urea aqueous solution used as a reducing agent as shown above.

Figure 3:
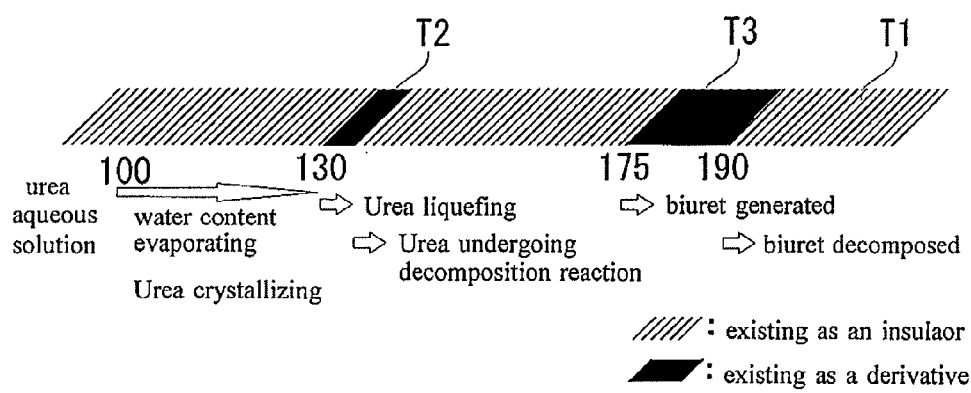
FIG. 3 illustrates changes in a state of the urea aqueous solution with respect to temperature.

FIG. 3 illustrates changes in a state of the urea aqueous solution used as a sample with respect to temperature. As shown in FIG. 3, the sample is sufficiently decomposed as in the above formulae (1) and (2) to produce the ammonia in a temperature range of about 190° C. or higher.

At low temperatures of about 100° C. or lower, the sample exists as the urea aqueous solution; however, at a temperature of more than 100° C., water content evaporates to leave crystallized urea. At this time, the sample exists as an insulator. Urea liquefies at a temperature reaching about 130° C. At about 135° C., the sample starts undergoing the thermal decomposition reaction (above formula (1)). In a second temperature range T2 of about 130 to 135° C. in FIG. 3, the urea turns to a liquid state. At this time, the sample exists as a derivative. With the temperature reaching about 135° C., the urea vaporizes to develop the state of formula (1) above, in which the sample is again an insulator.

At a temperature of about 160° C., the urea reacts with isocyanic acid and generation of biuret ($C_2H_5N_3O_2$) starts. Further, the sample containing the biuret turns to a liquid in a third temperature range T3 of about 175 to 190° C., becoming a conductor. When the temperature reaches about 190° C. thereafter, the biuret is decomposed. In a first temperature range T1 of about 190° C. or higher, the sample is an insulator.

Through the foregoing changes, if the urea aqueous solution in a condition of insufficiently undergoing the thermal decomposition reaction (1) or the hydrolysis reaction (2) is supplied to the NOx catalyst 12, the urea and the urea-derived substance (hereinafter referred to also as the "urea-related substance"), including the urea aqueous solution, the isocyanic acid, and the biuret, may be discharged downstream of the NOx catalyst 12. It is noted that, in the embodiments to be described below, the urea-related substance derived from the urea aqueous solution is not contained in the PM derived from the operation of the internal combustion engine 2 described above and will be differentiated from the PM.

If the discharged urea-related substance is in a condition of having conductivity, in particular, as described above, and is deposited on the electrodes 20, 22 of the PM sensor 14, the sensor output is likely to change sharply. The change in the sensor output in this case has no longer correlation with the actual amount of PM deposited in the exhaust gas. In such a case, therefore, it becomes difficult to make, for example, the determination of a fault of the DPF 6 with high accuracy and stably.

In the first embodiment, therefore, if it is estimated that a condition develops in which the urea-related substance that can affect the sensor output is deposited on the element section of the PM sensor 14, control is performed to increase the temperature of the element section to a level at which the urea-related substance can be decomposed and removed. In the embodiments to be described below, the "condition in which the urea-related substance is deposited" refers to, as the case may be, a condition in which the urea-related substance that can affect the sensor output is deposited.

The control according to the first embodiment specifically heats the element section of the PM sensor 14 to a temperature that falls within the first temperature range T1, which is higher than the temperature at which the biuret is decomposed and lower than the temperature at which PM starts burning. More preferably, the element section is heated to a temperature that falls within a range that is higher than and close to 190° C. PM burns at about 300° C.; however, removal of the PM deposited on the element section may result in an error in detection of a fault of the DPF 6. In addition, a high element section temperature degrades detecting performance of the sensor. To avoid excessive temperature increase, therefore, the temperature is set to a level that is higher than, and close to, the temperature at which the biuret is decomposed (190° C.).

The "condition in which the urea-related substance is deposited" can be estimated based on an amount of change in the sensor output. As described earlier, if the urea-related substance affecting the sensor, specifically, the urea-related substance existing as the conductor is deposited between the electrodes 20, 22 of the PM sensor 14, the change in conductivity across the electrodes 20, 22 greatly changes the resistance thereacross, so that the sensor output changes greatly. This change is a sharp and large one as compared with a mild change in the sensor output occurring as a result of the deposited PM.

In the first embodiment, therefore, whether the "condition in which the urea-related substance is deposited" develops is determined based on whether a gradient detected of a change in the sensor output over certain time is greater than a first reference value Ref1. The first reference value Ref1 is a value greater than an upper limit value in a range of a gradient of the output change occurring normally when PM is deposited and closer to a lower limit value in a range of the change occurring as a result of deposition of the urea-related substance having conductivity. An optimum value for the first reference value Ref1 is found in advance through, for example, experiments and stored in the control unit 16.

Figure 4:
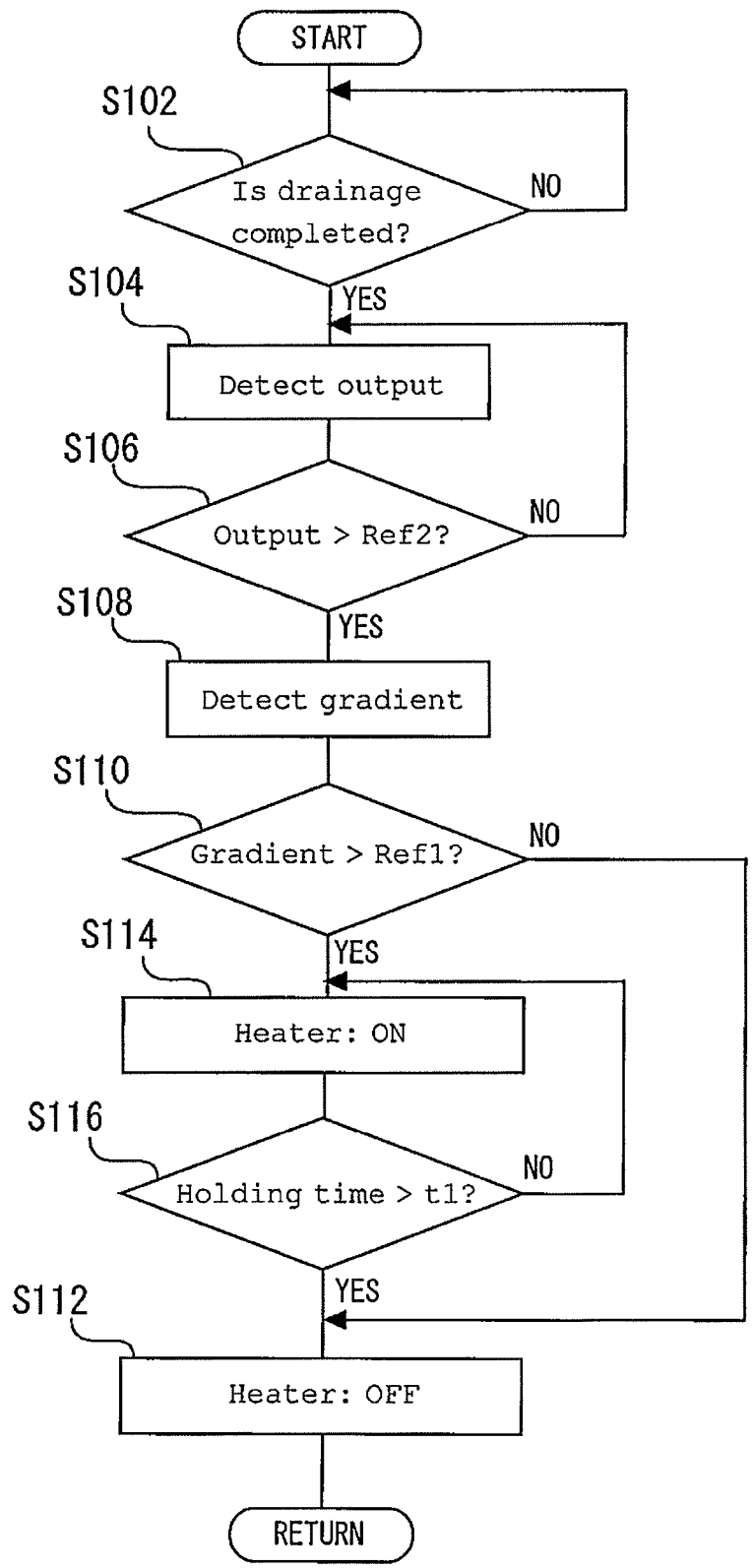
FIG. 4 is a flow chart illustrating a routine of the control performed by the control unit in the first embodiment of the present invention.

FIG. 4 is a flow chart illustrating a routine of the control performed by the control unit in the first embodiment of the present invention. The routine shown in FIG. 4 is repeatedly performed at every predetermined period of time during the operation of the internal combustion engine 2. In the routine shown in FIG. 4, it is first determined whether drying and drainage of the exhaust passage 4 is completed after starting of the internal combustion engine 2 (S102). To prevent the PM sensor 14 from developing element cracking, the PM sensor 14 must be put to use after the drying and drainage of the exhaust passage 4 is completed. Time should therefore be waited before the drying and drainage of the exhaust passage 4 is completed after the start of the internal combustion engine 2. The determination process of step S102 is therefore repeatedly performed every predetermined period of time until the completion of the drying and drainage is acknowledged in step S102.

When the completion of the drying and drainage is acknowledged in step S102, the sensor output of the PM sensor 14 is next detected (S104) and it is then determined whether the sensor output reaches a second reference value Ref2 (S106). The second reference value Ref2 is a value close to a lower limit value of the output produced when a certain amount of PM is deposited between the electrodes 20, 22 of the PM sensor 14 and a condition develops in which a sensor output corresponding to the amount of PM deposited is stably obtained. This value is found in advance through, for example, experiments and stored in the control unit 16. When the sensor output falls short of the second reference value Ref2, the sensor output varies greatly, which makes it difficult to determine a fault of the DPF 6 stably. When sensor output > second reference value Ref2 does not hold in step S106, the process returns to step S104 and the detection of the sensor output and the determination based thereon of steps S104 to S106 are performed again.

When sensor output > second reference value Ref2 holds in step S106, the gradient of the current sensor output is next calculated (S108). Specifically, the sensor output for a predetermined period of time is continuously detected after sensor output > second reference value Ref2 holds and an average gradient of the change in the sensor output during this period is calculated.

It is next determined whether the gradient of the change in the sensor output calculated in step S108 is greater than the first reference value Ref1 (S110). The first reference value Ref1 is stored in advance in the control unit 16 as described earlier, serving for determining the condition in which the urea-related substance is deposited on the element section. When, in step S110, sensor output change gradient > first reference value Ref1 does not hold, deposition of the urea-related substance is not acknowledged. Specifically, the sensor output is determined to correspond to the PM amount. The heater is therefore kept in an OFF position (S112) and the current routine is terminated. In this case, a process of, for example, determining a fault of the DPF 6 based on the sensor output, performed according to another control program is continued.

When, on the other hand, sensor output change gradient > first reference value Ref1 holds in step S110, the sensor output change is faulty and it is estimated that the condition develops in which the urea-related substance is deposited on the element section. In this case, to remove the urea-related substance deposited on the element section of the PM sensor 14, heating of the element section is started (S114). Specifically, the supply of electricity to the heater of the PM sensor 14 is turned ON.

It is next determined whether a holding time since the heating of the element section is started is longer than a reference time t1 (S116). The reference time t1 is a sufficient period of time during which the element section is heated to the first temperature range T1 of the biuret decomposition temperature and the biuret is completely decomposed. The time is found through, for example, experiments and stored in advance in the control unit 16. When holding time > reference time t1 does not hold in step S116, the process returns to step S114, and the condition in which the heater is ON (S114) is maintained and the determination of step S116 is made again.

When, on the other hand, holding time > reference time t1 holds in step S116, it is determined that the urea-related substance deposited on the element section is removed. In this case, the heater is next turned OFF (S112). The current routine is thereafter terminated and a process of, for example, determining a fault of the DPF 6 based on the sensor output and performed according to another control program is continued.

As described heretofore, in the first embodiment, the condition in which the urea-related substance is deposited can be estimated. Additionally, when the urea-related substance is estimated to be deposited, the urea-related substance having conductivity can be removed by heating the element section.

Figure 5:
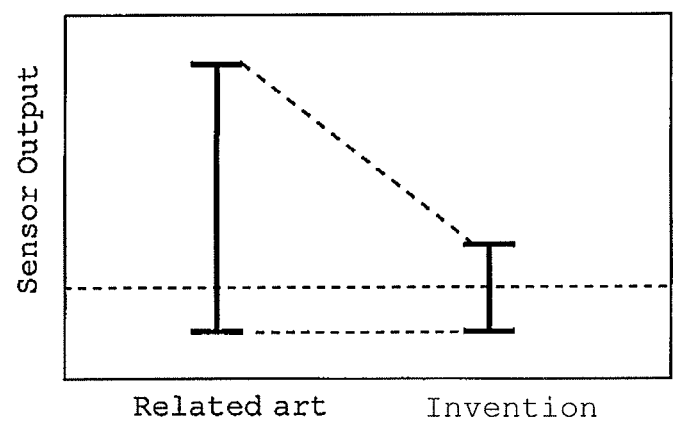
FIG. 5 compares variations in the sensor output according to the first embodiment of the present invention with those in the sensor output according to the related art.

FIG. 5 compares variations in the sensor output according to the first embodiment with those in the sensor output according to the related art when both detect gas with the same PM amount. Referring to FIG. 5, the variations in the sensor output can be limited by removing the urea-related substance from the element section at appropriate timing through the control according to the first embodiment. The system according to the first embodiment can therefore, for example, determine a fault of the DPF 6 stably.

Additionally, in the first embodiment, the element section of the PM sensor 14 is heated only when the urea-related substance is estimated to be deposited and the temperature to which the element section is heated is close to the decomposition temperature of the biuret as a urea-related substance (the first temperature range T1). This prevents detection accuracy from being degraded as a result of overheating the element section of the PM sensor 14.

The first embodiment has been described for a case in which deposition of the urea-related substance on the PM sensor 14 is estimated based on the gradient of the change in the sensor output. Nonetheless, in the present invention, the condition in which the urea-related substance is deposited may still be estimated using another technique.

In addition, the present invention has been described for a case in which the routine shown in FIG. 4 is repeatedly performed during operation of the internal combustion engine 2. This is, however, not the only possible arrangement for the present invention. The routine shown in FIG. 4 may be performed only during a specific period of time after the start of the internal combustion engine 2; for example, while the PM amount is being detected, while a fault of the DPF 6 is being determined, or during starting of the internal combustion engine 2, particularly while the exhaust passage 4 or the element section remains cold.

Second Embodiment

A system and a PM sensor 14 according to a second embodiment share the same arrangements with those of the first embodiment. The system of the second embodiment performs the following type of control in addition to those of the first embodiment.

As in the first embodiment, when the urea-related substance is estimated to be deposited based on the gradient of the change in the sensor output, it is then estimated that the urea-related substance is discharged downstream of a NOx catalyst 12. One possibility of the urea-related substance being discharged downstream of the NOx catalyst 12 is purification performance of the NOx catalyst 12 degraded by PM discharged downstream of a DPF 6 being deposited on the NOx catalyst 12. When a condition is acknowledged in which the urea-related substance is deposited, therefore, control is then performed in the second embodiment to remove the PM deposited on the NOx catalyst 12.

Specifically, the process for removing the PM deposited on the NOx catalyst 12 is performed by performance of a process for regenerating the DPF 6. Specifically, performing the process for regenerating the DPF 6 allows an exhaust gas at high temperature to flow also into the NOx catalyst 12, so that the PM deposited on the NOx catalyst 12 can be removed.

It is noted that, in the second embodiment too, deposition of the urea-related substance is estimated based on a magnitude of the change in the sensor output. It is, however, possible that the change in the sensor output is attributable to variations due to other factors not concerned with the urea-related substance.

In the second embodiment, therefore, when the urea-related substance is estimated to be deposited in, for example, a given session for determining deposition of the urea-related substance, specifically, when the gradient of the change in the sensor output is greater than the first reference value Ref1, a process is first performed to increase the temperature of the element section as in the first embodiment. Then, when the urea-related substance is estimated, a second time, to be deposited in a subsequent session for determining deposition of the urea-related substance, it is then acknowledged that the urea-related substance flows downstream of the NOx catalyst 12 and the process for regenerating the DPF 6 is performed. Specifically, in the second embodiment, the process for regenerating the DPF 6 is performed only when the urea-related substance is estimated to be deposited two consecutive times.

Figure 6:
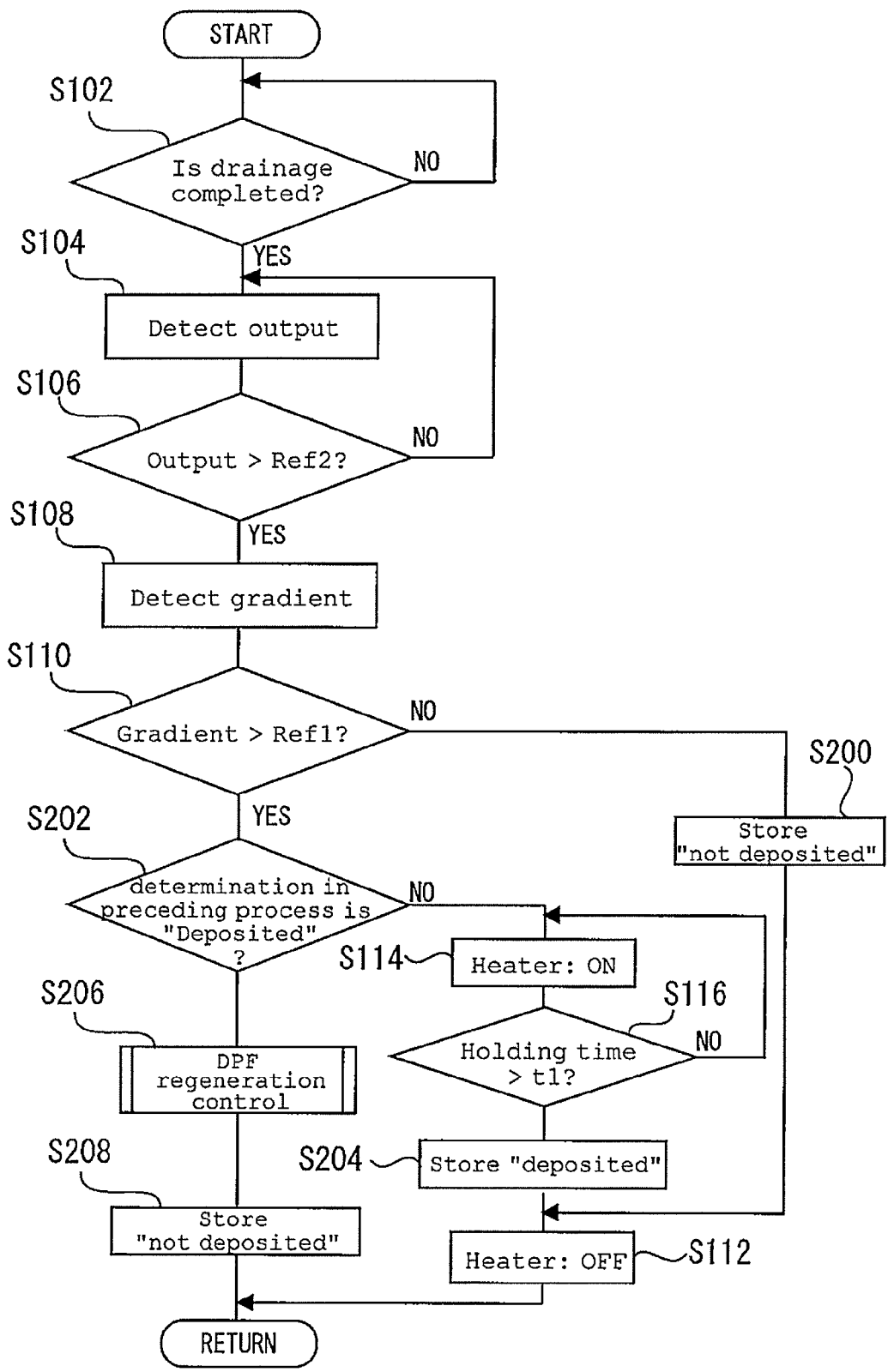
FIG. 6 is a flow chart for illustrating a routine of the control performed by a control unit in the second embodiment of the present invention.

FIG. 6 is a flow chart for illustrating a routine of the control performed by a control unit in the second embodiment of the present invention. The routine shown in FIG. 6 is the same as that shown in FIG. 4 except that processes of S200 to S208 are incorporated after the process of S110 in the routine shown in FIG. 4.

In the routine shown in FIG. 6, the processes of steps S102 to S110 are performed as described with reference to the routine of FIG. 4. When it is not acknowledged in step S110 that the gradient of the change in the sensor output is greater than the first reference value Ref1, a result of the determination for the current session is stored as "urea-related substance not deposited" (S200). Thereafter, the heater is turned OFF and the current routine is terminated as is in the same manner as in FIG. 4.

When, on the other hand, it is acknowledged in step S110 that the gradient of the change in the sensor output is greater than the first reference value Ref1, it is then determined whether the result of the determination in step S110 for the preceding session was "urea-related substance deposited" (S202). The result of the determination in step S110 for the preceding session is stored, as the case may be, in the control unit 16 during the preceding session.

When it is not acknowledged in step S202 that the preceding session was determined to be "urea-related substance deposited", the processes of S114 and S116 are performed as in the routine of FIG. 4 and, thereafter, the result of the determination for the current session is stored as "urea-related substance deposited" (S204).

Thereafter, the process of S112 is performed and the current routine is terminated. Specifically, a condition of the heater being energized is maintained for a reference time t1 (S114, S116). This increases the element section to be heated to the first reference value Ref1, so that the urea-related substance between electrodes 20, 22 is removed. The heater is thereafter turned OFF (S112) and the current routine is terminated.

If, on the other hand, it is acknowledged in step S202 that the preceding session was determined to be "urea-related substance deposited", a process for regenerating the DPF 6 is next performed (S206). The regeneration process for the DPF 6 is performed according to a control program stored in a control unit 16 separately from this routine. In this regeneration process for the DPF 6, a PM reset is also performed after completion of the regeneration process.

After the performance of the regeneration process for the DPF 6, therefore, the result of the determination for step S110 of the current session is stored as "urea-related substance not deposited" (S208). The current routine is thereafter terminated and the PM sensor 14 is put to use according to each control program, as in, for example, continued ordinary measurement.

As described above, in the second embodiment, when the urea-related substance is estimated to be deposited two consecutive times, the process for regenerating the DPF 6 is performed to thereby remove PM deposited on the NOx catalyst 12. This allows an SCR system 8 to recover its purification performance, thus preventing the urea-related substance from being discharged downstream.

The second embodiment has been described for a case in which, to remove the PM from the NOx catalyst 12, the process for regenerating the DPF 6 to thereby increase the temperature of the exhaust gas is performed. This is, however, not the only possible technique for removing the PM deposited on the NOx catalyst 12 in the present invention; alternatively, another technique that can efficiently remove the PM may be used. The technique used alternatively for regenerating the DPF 6 may be one that simultaneously removes the PM from the NOx catalyst 12; or, regardless of the regeneration of the DPF 6, the process for removing the PM from the NOx catalyst 12 may be independently performed by, for example, increasing the temperature of only the NOx catalyst 12.

In addition, the second embodiment has been described for a case in which the PM is removed from the NOx catalyst 12, only when the urea-related substance is determined to be deposited two consecutive times. This is, however, not the only possible arrangement. Alternatively, for example, when the urea-related substance is once determined to be deposited in S110 of the routine shown in FIG. 6, the process of step S202 is not performed and, instead, the process for removing the PM from the NOx catalyst 12 may be immediately performed, including, for example, the DPF 6 regeneration control. Alternatively, the DPF 6 regeneration control may be performed, only when the urea-related substance is determined to be deposited three consecutive times or more, instead of two consecutive times.

Third Embodiment

A system and a PM sensor according to a third embodiment share the same arrangements with those shown in FIGS. 1 and 2. The system of the third embodiment performs the following type of control in addition to those of the first embodiment.

When the urea-related substance is estimated to be deposited in a given session for determining deposition of the urea-related substance in the first embodiment, specifically, when the gradient of the change in the sensor output is greater than the first reference value Ref1, a process for increasing the temperature of the element section is performed for that particular session as in the first embodiment. In this case, it is anticipated that, in a subsequent session, an environment in which the urea-related substance is still discharged will develop. Therefore, when deposition of the urea-related substance is acknowledged in the preceding session, the determination of a fault of the DPF 6 for the current session is made in a condition in which the urea-related substance is not deposited, with the element temperature maintained at T1.

When, as a result, the same result of determination of a fault as in the preceding session is obtained, for example, it is confirmed that the PM sensor 14 and the determination result are correct. When the determination in the first session differs from that in the second session, variations in the output of the PM sensor 14 are considered to be attributable to a faulty PM sensor 14 or other factor, not affected by the urea-related substance. In this case, the determination of a fault of the DPF 6 may also be false. Therefore, in this case, a PM reset or other necessary control is performed.

Figure 7:
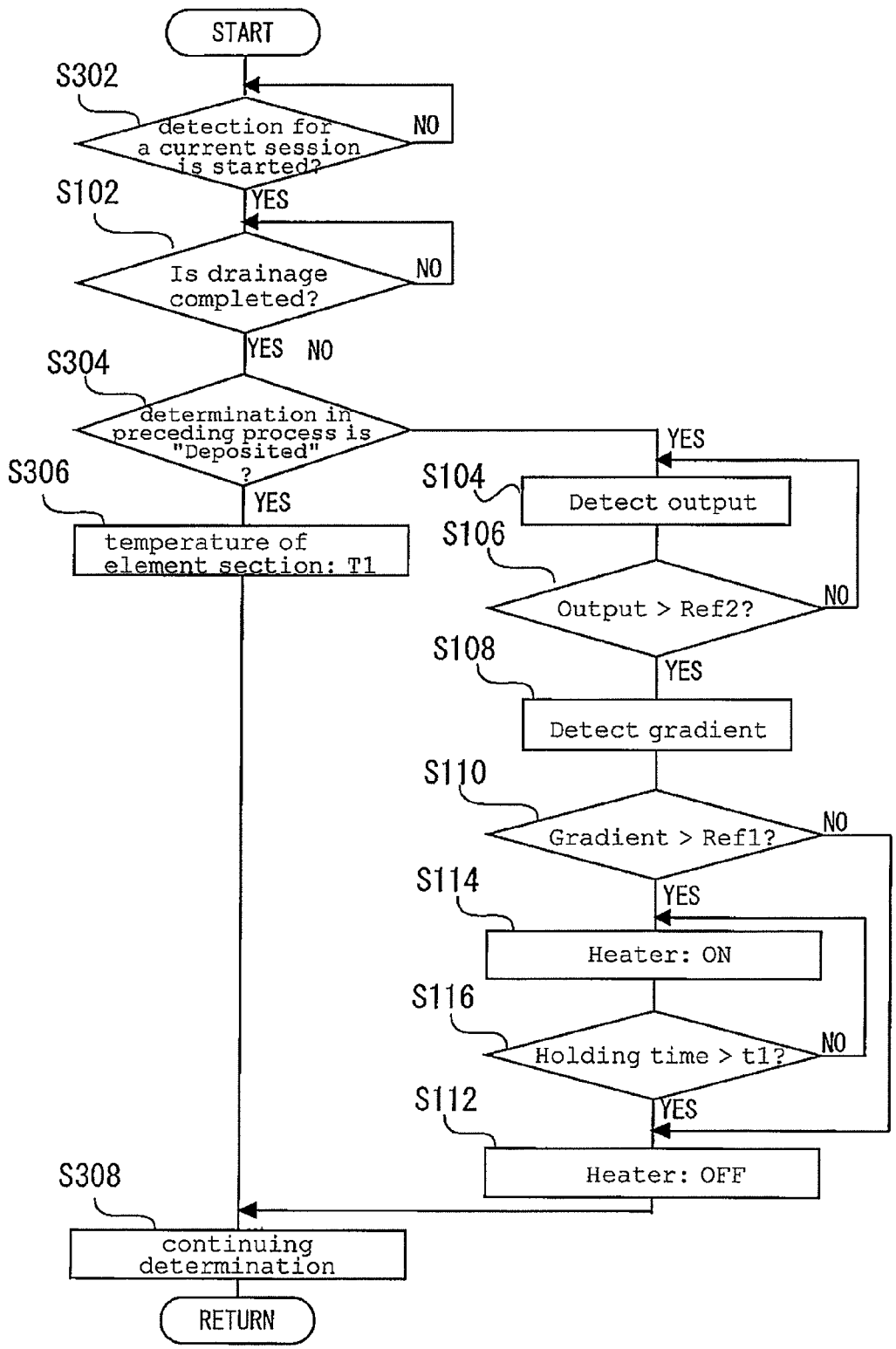
FIG. 7 is a flow chart for illustrating a routine of the control performed by a control unit in the third embodiment of the present invention.

FIG. 7 is a routine of the control performed by a control unit 16 in the third embodiment of the present invention. The routine shown in FIG. 7 is the same as that shown in FIG. 4 except that processes of S302 to S306 are incorporated. In this routine, it is first determined whether detection of the sensor output for a current session of fault determination is started (S302). The process of step S302 is repeatedly performed until it is determined that the detection of the sensor output is started.

When it is determined in step S302 that the detection of the sensor output is started, it is next determined whether drainage is completed (S102). When the process of drainage and drying of an exhaust passage 4 is not completed, the process is returned to step S102. Specifically, the process of step S102 is repeatedly performed until the drainage is completed.

It is next determined whether "urea-related substance deposited" is determined in the determination of a preceding routine (S304). Specifically, it is determined whether the gradient of the change in the sensor output is acknowledged to be greater than a first reference value Ref1 in the preceding routine. The result of determination in the preceding routine is stored in a control unit 16.

When "urea-related substance deposited" is not acknowledged in the preceding session in step S304, processes of steps S104 to S116 and S112 are then performed in the same manner as in FIG. 4. Specifically, the gradient of the sensor output is detected and, when the gradient is greater than the first reference value Ref1, the element section is heated to a first temperature range. The result of step S110 is stored in the control unit as a result of the current process.

When the urea-related substance deposited is acknowledged to be deposited in step S304, the temperature of the element section is maintained at the first temperature range T1 (S306). It is noted that the first temperature range T1 is a range of temperatures that are higher than the temperature at which the biuret as a urea-related substance is decomposed and lower than the temperature at which PM burns. Maintaining the element section in the first temperature range T1 allows the urea-related substance deposited on the element section to be removed and an effect of the urea-related substance having conductivity on the sensor output to be precluded. Under this condition, the determination of a fault of the DPF 6 is placed in a continued state according to a control program stored in the control unit 16 separately and the current routine is terminated.

Thereafter, it is determined whether, for example, the result of determination of a fault of the DPF 6 in the preceding session is the same as that in the current session according to another control program. This achieves enhanced accuracy in determining a fault of the DPF 6.

The third embodiment has been described for a case in which, when the urea-related substance is acknowledged to be deposited in the preceding session, the PM amount is detected in the current session with the element temperature maintained in the first temperature range T1. This is, however, not the only possible arrangement for the present invention. Alternatively, for example, in determining a fault in the preceding session, instead of step S304, it is determined whether the DPF 6 has been determined to be faulty; and when the DPF 6 has been determined to be faulty, the element temperature may then be controlled to fall within the first temperature range T1. In this case too, the result of determination of a fault in the preceding session can be confirmed again in a condition in which the effect of the deposited urea-related substance is limited. This achieves an even higher accuracy in detecting a fault of the DPF 6.

Fourth Embodiment

A system and a PM sensor according to a fourth embodiment share the same arrangements with the system and the PM sensor shown in FIGS. 1 and 2. In the system of the fourth embodiment, in addition to the process for removing the urea-related substance when it deposited, as described in the first embodiment, a process for maintaining a condition in which the urea-related substance is not deposited is performed.

It is here noted that, when, for example, an intake air amount Ga is large, the flow rate of the exhaust gas increases, so that the urea-related substance tends to be discharged downstream of an SCR system 8. Similarly, when a urea equivalence ratio is high, specifically, when a large amount of urea is injected, or when the temperature of a NOx catalyst 12 is low, the urea-related substance tends to be discharged downstream of an SCR system 8.

In the system of the fourth embodiment, therefore, in an environment as described above in which the urea-related substance is expected to be discharged, a process is performed in advance to limit deposition of the urea-related substance on an element section. Specifically, under an operating condition in which the amount of the urea-related substance to be discharged is expected to increase, the temperature of the element section is controlled so as not to fall within the second temperature range T2 of 130 to 135° C. representing a liquidus temperature of the urea and the third temperature range T3 of 175 to 190° C. representing the biuret decomposition temperature range. Deposition of a conductive urea-related substance, in particular, that affects the sensor output can thereby be prevented in advance, so that variations in the sensor output can be limited.

Figure 8:
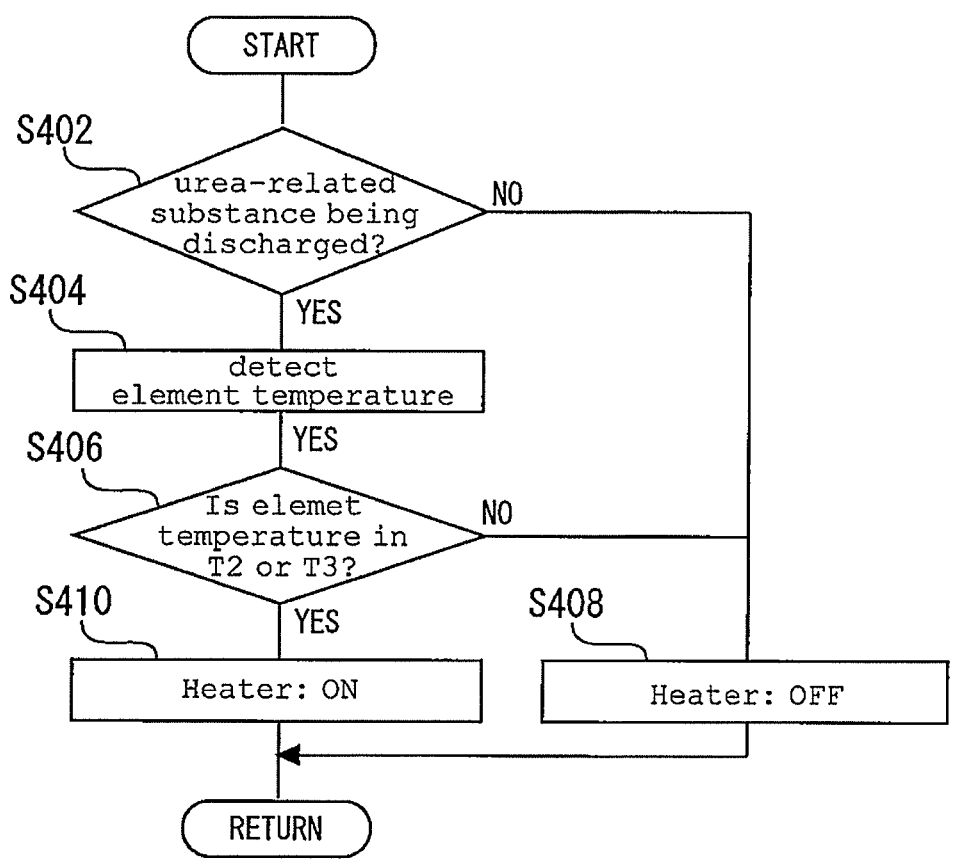
FIG. 8 is a flow chart for illustrating a routine of the control performed by a control unit in the third embodiment of the present invention.

FIG. 8 is a flow chart illustrating a routine of control performed by a control unit in the fourth embodiment of the present invention. The routine shown in FIG. 8 is performed prior to the routine shown in FIG. 4. Specifically, in the routine shown in FIG. 8, it is first determined whether the current operating condition is such that the urea-related substance is expected to be discharged (S402). The condition for the operating condition in which the urea-related substance is expected to be discharged is defined and stored in advance in the control unit 16. Thus, it is here determined whether the operating condition satisfies the condition stored in the control unit 16.

When it is not determined in step S402 that the urea-related substance is expected to be discharged, the current routine is terminated. When it is determined in step S402 that the urea-related substance is expected to be discharged, on the other hand, the current element temperature is next detected (S404). The element temperature is detected by detecting resistance of the heater.

It is then determined whether the element temperature falls within the second temperature range T2 or the third temperature range T3 (S406). The temperature range T2 represents the liquidus temperature range of the urea and the temperature range T3 represents the biuret decomposition temperature range. When it is not determined in step S406 that the temperature falls within the second temperature range T2 or the third temperature range T3, the heater is turned OFF (S408). The current routine is thereafter terminated.

When it is determined in step S406 that the temperature falls within the second temperature range T2 or the third temperature range T3, on the other hand, the heater is then energized to thereby heat the element section (S410). When, for example, the temperature falls within the second temperature range T2, the element temperature is controlled to fall within a range higher than the second temperature range T2 and lower than the third temperature range T3, or the first temperature range T1 that is higher than the third temperature range T3. Alternatively, when the element temperature falls within the third temperature range T3, the element temperature is controlled to fall within the first temperature range T1. This prevents the urea-related substance in a conductor state from being deposited on the element section. The current routine is thereafter terminated.

In the fourth embodiment, following the completion of the above-described routine shown in FIG. 8, the routine shown in FIG. 4 is continuously performed. Even in an environment in which the urea-related substance is easily discharged, control is here performed in advance to ensure that the urea-related substance is less easily deposited on the element section. In step S110, therefore, it is more likely to be determined that the urea-related substance is not deposited (specifically, output change gradient > first reference value Ref1 is likely to be determined not to hold). In this case, measurement of the PM amount and the determination of a fault of the DPF 6 based thereon can be efficiently made to proceed.

The present invention is not, however, limited to a case in which the routine shown in FIG. 4 follows immediately the routine shown in FIG. 8. The control according to the fourth embodiment described with reference to FIG. 8 may be performed independently as appropriate, regardless of FIG. 4, in an environment in which deposition of the urea-related substance is not desirable. This effectively prevents the urea-related substance existing in a conductor state from being deposited on the element section of the PM sensor 14 as necessary.

Any number, quantity, amount, range, or the like mentioned for each element in the above descriptions of the embodiments should not be construed as limitative unless expressly specified or specifically defined in principle. In addition, structures, manufacturing steps, and the like described in the embodiments should not be construed as essential to the present invention unless expressly specified or specifically defined in principle.

DESCRIPTION OF NOTATIONS 2 internal combustion engine
4 exhaust passage
8 SCR system
10 injection valve
12 NOx catalyst
14 PM sensor
16 control unit
18 insulating substrate
20, 22 electrode
Ref 1 first reference value
Ref 2 second reference value
T1 first temperature range
T2 second temperature range
T3 third temperature range
t1 reference time

The invention claimed is:

1. An internal combustion engine comprising:
a selective catalytic reduction (SCR) system disposed on an exhaust passage;
a particulate matter sensor disposed downstream of the SCR system, the particulate matter sensor producing an output that corresponds to an amount of particulate matter deposited on an element section, the particulate matter sensor comprising a heater; and
a control unit programmed to:
estimate a condition of the element section being deposited with a urea-related substance; and
control the heater to bring a temperature of the element section to a first temperature range when the condition of being deposited with the urea-related substance is estimated, the first temperature range being (i) higher than a temperature at which the urea-related substance vaporizes and (ii) lower than a temperature at which the particulate matter burns.

2. The internal combustion engine according to claim 1, wherein the control unit is further programmed to estimate the condition of being deposited with the urea-related substance based on an amount of change in an output of the particulate matter sensor.

3. The internal combustion engine according to claim 2, wherein the control unit is further programmed to remove particulate matter deposited on a catalyst of the SCR system when the condition of being deposited with the urea-related substance is estimated.

4. The internal combustion engine according to claim 1, wherein the control unit is further programmed to remove particulate matter deposited on a catalyst of the SCR system when the condition of being deposited with the urea-related substance is estimated.

5. The internal combustion engine according to claim 4, further comprising:

a filter disposed upstream of the particulate matter sensor along the exhaust passage, the filter trapping particulate matter contained in an exhaust gas, wherein the control unit is further programmed to remove particulate matter deposited on the catalyst by performing a process for removing particulate matter accumulated on the filter.

6. The internal combustion engine according to claim 4, wherein the control unit is further programmed to remove the particulate matter by performing a control of increasing a temperature of the exhaust gas of the internal combustion engine.

7. The internal combustion engine according to claim 4, wherein the control unit is further programmed to remove the particulate matter when the estimating means estimates the condition of being deposited with the urea-related substance a plurality of times consecutively.

8. The internal combustion engine according to claim 1, further comprising:

a filter disposed upstream of the particulate matter sensor along the exhaust passage, the filter trapping particulate matter contained in an exhaust gas, wherein the control unit is further programmed to:

store a history of the estimation of the condition of being deposited with the urea-related substance, if a latest estimation in the history indicates that the condition of the element section being deposited with the urea-related substance has occurred, control the heater to increase the temperature of the element section to fall within the first temperature range and determine whether the filter is faulty based on the output of the particulate matter sensor under a temperature condition in which the temperature of the element section is controlled to fall within the first temperature range without performing the estimation; and if the latest estimation in the history indicates that the condition of the element section being deposited with the urea-related substance has not occurred, perform the estimation of the condition of the element section being deposited with the urea-related substance, and determine whether the filter is faulty based on the output of the particulate matter sensor after performing the estimation.

9. The internal combustion engine according to claim 1, further comprising:

a filter disposed upstream of the particulate matter sensor along the exhaust passage, the filter trapping particulate matter contained in an exhaust gas, wherein the control unit is further programmed to:

determine whether the filter is faulty based on the output of the particulate matter sensor, store a history of the determination of the fault of the filter, if a latest determination in the history indicates that the filter has been faulty, control the heater to increase the temperature of the element section to fall within the first temperature range and perform the determination of the fault of the filter under a temperature condition in which the temperature of the element section is controlled to fall within the first temperature range without performing the estimation; and if the latest determination in the history indicates that the filter has not been faulty, perform the estimation of the condition of the element section being deposited with the urea-related substance, and perform the determination of the fault of the filter based on the output of the particulate matter sensor after performing the estimation.

10. The internal combustion engine according to claim 1, wherein:

the control unit is further programmed to:

detect whether or not an operation state of the internal combustion engine is in a predetermined operating condition in which the urea-related substance is discharged to the exhaust passage, and control the heater, in a case of the predetermined operating condition being detected, such that the temperature of the element section (i) is brought to a temperature that falls outside a urea liquidus temperature range and a biuret decomposition temperature range and (ii) is lower than a temperature at which particulate matter burns.

11. The internal combustion engine according to claim 1, wherein the SCR system comprises a NOx catalyst and an injection valve to inject a urea aqueous solution upstream of a NOx catalyst.

12. An internal combustion engine system comprising:

an internal combustion engine;

a selective catalytic reduction (SCR) system disposed on an exhaust passage;

a particulate matter sensor disposed downstream of the SCR system, the particulate matter sensor produces an output that corresponds to an amount of particulate matter deposited on an element section, the particulate matter sensor comprising a heater; and a control unit programmed to:

detect whether or not an operation state of the internal combustion engine is in a predetermined operating condition in which the urea-related substance is discharged to the exhaust passage, and control the heater, in a case of the predetermined operating condition being detected, such that a temperature of the element section is brought to a temperature that (i) falls outside a urea liquidus temperature range and a biuret decomposition temperature range and (ii) is lower than a temperature at which particulate matter burns.

13. The internal combustion engine according to claim 12, wherein the SCR system comprises a NOx catalyst and an injection valve to inject a urea aqueous solution upstream of a NOx catalyst.

* * * * *